United States Patent [19]
Hasseberg et al.

[11] Patent Number: 5,976,609
[45] Date of Patent: Nov. 2, 1999

[54] PROCESS FOR RECOVERING 2-HYDROXY-4-METHYLTHIOBUTYRIC ACID (MHA), MHA AND ITS USE

[75] Inventors: Hans-Albrecht Hasseberg, Rodenbach; Klaus Huthmacher, Gelnhausen; Herbert Tanner, Hanau; Volker Häfner, Langenselbold; Harald Heinzel, Frankfurt am Main, all of Germany

[73] Assignee: Degussa Aktiengesellschaft, Frankfurt, Germany

[21] Appl. No.: 08/776,217

[22] PCT Filed: Jun. 28, 1995

[86] PCT No.: PCT/EP95/02515

§ 371 Date: Jan. 13, 1997

§ 102(e) Date: Jan. 13, 1997

[87] PCT Pub. No.: WO96/01809

PCT Pub. Date: Jan. 25, 1996

[30] Foreign Application Priority Data

Jul. 11, 1994 [DE] Germany ............... 44 24 043

[51] Int. Cl.⁶ .............. A23L 1/305; A23L 1/28; C15C 315/02; C15C 315/06
[52] U.S. Cl. .............. 426/648; 426/425; 426/655; 426/807; 426/656; 562/581; 514/557
[58] Field of Search .............. 426/425, 648, 426/655, 807, 656; 562/581; 514/557

[56] References Cited

U.S. PATENT DOCUMENTS

| | | | |
|---|---|---|---|
| 3,175,000 | 3/1965 | Gielkins | 260/535 |
| 4,524,077 | 6/1985 | Ruest et al. | 514/557 |
| 4,912,257 | 3/1990 | Hernandez et al. | 562/281 |

FOREIGN PATENT DOCUMENTS

142 488    5/1985    European Pat. Off. .

*Primary Examiner*—Frank C. Eisenschenk
*Assistant Examiner*—M K Zeman
*Attorney, Agent, or Firm*—Pillsbury Madison & Sutro LLP

[57] ABSTRACT

It is known to isolate MHA from a reaction mixture obtained by the addition of hydrocyanic acid (HCN) to methyl mercaptopropionic aldehyde (MMP) and the hydrolysis of the methyl mercapto propionic aldehyde cyanohydrine (MMP-CH) obtained thereby with sulphuric acid, in which the reaction mixture is brought into contact with a substantially non-water-miscible organic solvent, in order to form an extraction solution having the solvent and MHA transferred from the reaction mixture, and the MHA is obtained as an extract from this extraction solution by concentration. The simplest and most economical process of the invention concerning the processing of the reaction product which facilitates the production of a highly concentrated product with an extremely low dimer, oligomer and by-product content, is characterised in that the concentration is conducted in such a way that the remaining extract contains less than 4 wt % and preferably less than 2 wt % of water. Animal feed supplement, mixtures for supplementing animal feed, e.g. with methionine or ammonium-MHA.

8 Claims, 6 Drawing Sheets

PROCESS FOR RECOVERING 2-HYDROXY-4-METHYLTHIOBUTYRIC ACID (MHA), MHA AND ITS USE

This application is based on DE patent application Ser. No. 44240430 filed in Germany on Jul. 11, 1994 and PCT/EP95/02175 filed Jun. 28, 1995, the contents of which are incorporated hereinto by reference.

The invention relates to a process for recovering 2-hydroxy-4-methylthiobutyric acid (MHA), MHA obtainable in accordance with the invention and use of the MHA prepared by this process.

The invention relates in particular to an improved, new type of isolation process for MHA in very high concentration and purity from a reaction mixture resulting during preparation.

BACKGROUND OF THE INVENTION

2-hydroxy-4-methylthiobutyric acid (MHA) is the hydroxyl analogue of the essential amino acid methionin in racemic form and like the latter is an important additive in animal nutrition. When rearing poultry, MHA shows similar growth stimulating properties to those of the amino acid recognised for this purpose. The additive is also being used increasingly in other areas of animal nutrition.

MHA is mostly used in the form of aqueous concentrates, wherein these contain, in addition to the monomer, a certain proportion of oligomers, mainly dimeric and trimeric linear ester acids. The actual amount of these oligomers depends on the conditions of preparation and the concentration selected. Due to their low nutritive action and the inconvenient effect on the flow properties, due to an increase in viscosity, it is desirable, however, to keep their percentage proportion as low as possible. Commercial formulations preferably have, for a total concentration of 88–90 wt. %, up to 24 wt. %, corresponding to ca. 27 mol. % in total of oligomers, corresponding to a monomer/oligomer ratio of ~3:1.

Use of the calcium salt and mixed calcium ammonium salt of MHA as an animal feed additive is also known. Production of these salts, however, is associated with higher production costs. In addition, as powdered solids they are less easy to incorporate into the feedstuff formulation than readily sprayed aqueous concentrates of the free acids with low proportions of oligomers.

The synthetic route to MHA consists of 3 reactions.

The general process for preparing MHA starts from 3-methylthiopropionaldehyde, also called methylmercaptopropionaldehyde or MMP, which is reacted with hydrogen cyanide to give 2-hydroxy-4-methylthiobutyronitrile, also called MMP-cyanohydrin or MMP-CH (equation 1).

(I)

The MMP-cyanohydrin produced is then usually hydrolysed with strong inorganic acids via the intermediate stage of 2-hydroxy-4-methylthiobutyramide, also called MHA-amide (equation II), (II)

to give the methionin hydroxy analogue (MHA) (equation III).

(III)

This hydrolysis can be performed in either one or two stages, wherein "stages" is understood to mean that inorganic acid and/or water is added either once or twice to hydrolyse the MMP-CH, i.e. the number of stages corresponds to the number of addition processes.

A two-stage method of working starting from MMP-cyanohydrin is described in U.S. Pat. Nos. 2,745,745, 2,938,053 and 3,175,000. There, the cyanohydrin is initially reacted at relatively low temperatures with concentrated inorganic acids, e.g. with 50–85% strength sulphuric acid, to give MHA-amide, whereupon hydrolysis to give MHA is then performed at elevated temperature after the addition of water. The calcium or calcium ammonium salt of MHA and the coupled product calcium sulphate is obtained from this by treating the saponification mixture with calcium hydroxide or carbonate. To avoid the inevitable production of unwanted secondary products, the first two patents mentioned recommend using the hydrolysis reagent sulphuric acid in a sub-stoichiometric ratio to MMP-cyanohydrin of, for example, 0.55–0.8:1. British patent 722 024, which describes a similar method of forming the MHA salts from MHA-amide, also implies the two-stage method of working.

A two-stage hydrolysis is also used in the methods disclosed in European patents 0 142 488 (using sulphuric acid) and 0 143 100 (using inorganic acids), the object of which is the recovery of MHA in a liquid form, that is in highly concentrated aqueous solutions. These are obtained after the hydrolysis reaction, performed under defined concentration and temperature conditions via the amide stage using excess inorganic acids, by means of solvent extraction, wherein specific solvents which are partially miscible with water are used.

According to the data in these patents, the characterising feature of the method described therein is regarded as the recovery of MHA from the extraction solution, which is performed in such a way that recovery includes removal of the organic solvent in the presence of at least about 5 wt. % of water, with respect to the remaining extract (MHA). MHA is recovered from the extraction solution by distillation (see the examples), wherein steam distillation is preferred. By removing the solvent from the extraction solution during steam distillation, the bottom product obtained is a mixture of MHA and water. Steam distillation is therefore performed in such a way that the bottom product contains at least 5 wt. % of water.

At another point, the patents in question specify that the column conditions during distillation are controlled in such a way that throughout the column, at least, however, in the bottom fraction, the liquid phase contains about 5 wt. % of water.

From this, it follows that without the presence of a sufficient amount of water during recovery of MHA from the extraction solution the increasing formation of unwanted secondary products (dimers and oligomers) is to be feared.

Furthermore, the steam is used during distillation as a driving agent for complete removal of the extraction agent from the MHA solution, e.g. by forming a low-boiling azeotropic mixture with the corresponding extraction agent.

Concentrated MHA solutions without the use of a solvent are obtained according to U.S. Pat. No. 3,773,927 by means of a two-stage hydrolysis of MMP-cyanohydrin using excess aqueous hydrochloric acid, subsequent concentration of the saponification mixture and separation of the crystallised-out ammonium chloride. The MHA concentrates obtained in this way, however, smell of oligomers and are dark coloured. Also, the isolated ammonium chloride is heavily contaminated.

According to U.S. Pat. No. 4,353,924, the excess inorganic acid, after two-stage hydrolysis using hydrochloric acid, is neutralised with ammonia or another alkaline substance. Concentrated MHA solutions with very few corrosive properties are obtained in this way.

A process is described in U.S. Pat. No. 4,310,690 in which, after hydrolysis with hydrochloric acid the mixture is neutralised with caustic soda solution under precisely defined conditions and the ammonium chloride is converted into common salt and ammonia. During subsequent treatment with slaked lime, the MHA calcium salt is obtained as a slurry in a virtually saturated solution of common salt. After solid/liquid separation, the majority of the filtrate is recycled to prepare the slaked lime slurries. In this way, pollution of the effluent is reduced and the co-production of unwanted or environmentally polluting impurities is avoided.

One-stage hydrolysis methods are also described in the patent literature. Thus, the process according to British patent 915 193 is aimed at the recovery of the MHA calcium salt, wherein after saponification of MMP-cyanohydrin with excess dilute sulphuric acid, the MHA formed is separated from the saponification solution by means of extraction with high-boiling ethers and the MHA calcium salt is obtained by subsequent treatment of the extract with calcium hydroxide. Return of the aqueous raffinate to the saponification stage which is provided in this continuous process, however, leads to an accumulation of inorganic minor constituents.

European patent 0 330 527 discloses a further one-stage hydrolysis process using sulphuric acid as the saponification agent, which takes place without solvents and leads directly to concentrated aqueous MHA solutions, wherein crystalline ammonium sulphate in saleable form is obtained as the co-product. This objective is achieved by neutralising the saponification mixture with ammonium hydroxide solution until the excess inorganic acid and the ammonium bisulphate produced have been converted into the neutral sulphate, wherein two liquid phases are produced, which for their part can be separated and evaporated down in order to obtain MHA on the one hand and crystalline ammonium sulphate on the other hand. In this case, the various filtration and recovery steps are combined in such a way that virtually no product is lost and no salt-polluted effluent is produced. The resulting MHA is of similar quality to the product obtained according to EP 0 142 488.

However, even this environmentally friendly process has various disadvantages. As the applicant of the present invention established when reworking this process, as a result of the comparatively high dilution of the sulphuric acid (20–50%) a considerably higher excess of acid than stated has to be used in order to achieve complete cyanohydrin conversion. Also, to avoid the deposition of salt during neutralisation, high dilutions have to be used in order to be able to separate the two liquid phases cleanly. Next, the ammonium sulphate obtained is of a sticky consistency and associated with a penetrating odour so that aftertreatment, such as e.g. wash-filtration or recrystallisation is required, which increases the costs of the process. Again, the process consumes more energy in the evaporation steps than the process in EP-A 0 142 488 which is cited for comparison, differently than is asserted. Solids handling, arranged in two separate lines with filtering/centrifuging and, not shown in the flow-chart, drying of the ammonium sulphate, is also very costly and utilises complex equipment.

SUMMARY OF THE INVENTION

In view of the prior art cited herein and the disadvantages associated with known processes, the object of the invention is to provide a further process for the preparation of 2-hydroxy-4-methylthiobutyric acid (MHA) of the type mentioned at the beginning, which is intended to be as simple and cost effective as possible with regard to processing the reaction products and is intended to provide the most highly concentrated product possible with the lowest possible concentration of dimers, oligomers and secondary products. The invention thus provides data for an improved MHA and its use.

This is achieved along with further objects which are not stated in detail by a process for recovering 2-hydroxy4-methylthiobutyric acid (MHA) in which the MHA is isolated from a reaction mixture which is obtained by the addition of hydrocyanic acid (HCN) to methylmercaptopropionaldehyde (MMP) and hydrolysis of the thereby obtained methylmercaptopropionaldehyde cyanohydrin (MMP-CH) with sulphuric acid, wherein an organic solvent which is essentially immiscible with water is added to the reaction mixture in a liquid/liquid extraction system, in order to form an extraction solution which contains the solvent and MHA transferred from the reaction mixture, and the MHA is obtained as an extract from this extraction solution by evaporation, wherein the evaporation is performed in such a way that the remaining extract contains less than 4 wt. % of water.

Advantageous process embodiments involve removing the organic solvent in an evaporation process using a thin layer evaporator, a falling film evaporator or a short-path evaporator or an evaporator and/or a stripping stage. In another embodiment, the pressure during evaporation is not greater than 600 mbar. In yet another embodiment, the temperature of the MHA as an extract during evaporation is not essentially higher than 150° C. In another embodiment, the temperature of the MHA as an extract is between 30 and 100° C. at an outlet from the evaporation procedure. In another embodiment, the residence time of the remaining extract in the evaporation stage is not longer than 1.5 h.

In yet another embodiment, the hydrolysis of the MMP-CH is performed in such a way that in a first stage the MMP-CH is hydrolysed with 60–85% strength sulphuric acid in a molar ratio MMP-CH:$H_2SO_4$ of 1:0.5 to 1:1.05 at temperatures of 30–90° C. with the production of essentially MHA-amide. The MHA-amide produced is then hydrolysed in a second stage by adding water without the further addition of $H_2SO_4$, at temperatures of up to 140° C. In another embodiment the MHA obtained has more than 98 wt. % of MHA calculated as the sum of monomeric MHA, MHA dimers and MHA oligomers, as well as more than 0.1 and less than 2 wt. % of water, and a kinematic viscosity of >100 mm$^2$/s at 25° C. Another embodiment relates to use of MHA to prepare mixtures for supplementing animal feedstuffs, in which a mixture of methionin and MHA is prepared wherein the MHA content including monomers, dimers and oligomers is <80 wt. % and wherein the oligomer content including MHA dimers and oligomers is <25 mol-%, with respect to the total active substance content of MHA, dimers and oligomers and methionin, after storage for 300 days at room temperature. Yet another embodiment relates to a mixture for supplementing animal feedstuffs, wherein a mixture is prepared with gaseous ammonia, aqueous ammonia and/or ammonium MHA, in which the MHA content including monomers, dimers and oligomers is <80 wt. % and wherein the oligomer content including MHA dimers and oligomers is <25 mol-%, with respect to total active substance content of MHA, dimers and oligomers, after storage for 30 days at 40° C.

Since evaporation of the extraction solution to obtain MHA as product (remaining extract) is performed in such a way that the remaining extract contains less than 4 wt. %, preferably less than 2 wt. %, of water, the invention provides a process which enables the preparation of liquid MHA of outstanding quality and which in particular produces in an unforeseeable manner a highly concentrated liquid MHA with a low proportion of oligomers and dimers. From the point of view of the known processes in the prior art, in particular the two European patents 0 142 488 and 0 143 100, it has to be recognised as more than surprising that this can be achieved with smaller amounts of water than a person skilled in the art would infer from the patents mentioned. Within the scope of the invention, it was also, unforeseeably, shown that approximately 100% strength MHA solutions are obtainable which can be transported without any clear loss of quality and then adjusted to desired concentrations with suitable additives or diluents. This finding is an enormous economic advantage for a large-scale process.

DETAILED DESCIPTION OF THE INVENTION

The present invention is thus concerned with one important aspect, in particular the evaporation of an extraction solution, in the form in which it is obtained following liquid/liquid extraction of a reaction mixture which is obtained, for example, by hydrolysis of MMP-CH with sulphuric acid.

The extraction solution used for evaporation to recover MHA can be obtained from the reaction mixture by processes familiar to a person skilled in the art, for example by extraction. The organic solvent used for extraction in this process should be essentially immiscible with water. However, partial miscibility of the organic solvent with water can be tolerated. Among solvents which are suitable for material separation in the liquid/liquid extraction process are a number which satisfy the conditions of chemical inertness and a low solubility towards water. In general it is preferable that the solubility of water in the solvent should be not greater than ca. 15 wt. %, preferably not greater than 10 wt. %, at room temperature. From among the suitable solvents, those which are preferred have a boiling point between ca. 60° C. and ca. 200° C., preferably between ca. 70° C. and 150° C. The partition coefficient for MHA in equilibrium between the solvent, which contains the extracted MHA, and the aqueous raffinate, which remains behind after the solvent and the MHA hydrolysate are placed in contact, should be at least ca. 2. This partition coefficient should preferably be at least 5. Also, the partition coefficient for MHA in equilibrium between extraction solution and wash water should not be less than about 1. Furthermore, the solvent should have low toxicity.

A number of ketones, aldehydes and carboxylates are particularly suitable as a solvent in the extraction process. Particularly preferred solvents are ketones with comparatively low molecular weights such as, for instance, methyl-n-propyl ketone, methylethyl ketone, methylamyl ketone, methylisoamyl ketone, methylisobutyl ketone, ethylbutyl ketone and diisobutyl ketone. Highly suitable solvents for the extraction process are also aldehydes such as, for instance, n-butyraldehyde, and esters such as, for instance, ethyl acetate, n-butyl acetate, n-propyl acetate and isopropyl acetate. Alcohols may also be used, although these are less preferred due to their mutual solubility with water, slow phase separation and the tendency to react with MHA.

The extraction itself may basically be performed continuously or intermittently. For a batchwise process, a stirred tank reactor, for instance, is suitable. Preferably, however, the extraction is performed in a continuous countercurrent extraction plant which has an extraction zone designed to accelerate the mass transfer between solvent and aqueous phase. Thus, it is advantageous, for example, to perform the extraction in a cascade of continuous countercurrent mixer/separators, a packed column, a perforated plate column, preferably as a pulsed column or a column with movable perforated plates, a column with rotary plates or a centrifugal extractor. In a particularly preferred embodiment the extraction is performed in a perforated plate column for liquid/liquid extraction. Intermittent or pulsed currents, although cyclical and thus not continuous in the sense of rapid flow rates, are regarded as "continuous" in connection with the present disclosure.

The extraction process is preferably controlled in order to produce and maintain the solvent phase in the extraction zone as the continuous phase.

In order to keep the salt content of the final product to a minimum, the extract is preferably washed with water. In a continuous countercurrent extraction system, the extract can be washed by mixing with water at a point which is upstream, with reference to the direction of the organic current, of the point at which the hydrolysate is introduced into the liquid/liquid extraction system. Thus, for example, in a vertical column and using a solvent whose specific weight is preferably less than 1, solvent is introduced into the column at a point below the feed point at which the aqueous hydrolysate solution is introduced and wash water is introduced to the column at a point above the feed point for the hydrolysate solution. In a preferred embodiment, the solvent is supplied at a rate of about 0.5 to 0.6 parts by weight per unit of weight of hydrolysate, when an extract with a specific weight of about 0.92 to 0.97 and a total MHA concentration (total MHA=sum of MHA monomers, dimers+oligomers+optional MHA-amide) of 35 to 40 wt. % is obtained.

The productivity of the extraction process is increased by operating at a slightly elevated temperature, by providing a relatively low viscosity for the solvent phase within the extraction system. Operating at a temperature in the range of about 50 to about 80° C. also produces a slightly beneficial effect on the MHA partition coefficient between the organic and the aqueous phase.

In the scope of the invention, MHA can be recovered from the extraction solution by evaporation, as already mentioned. In a particularly preferred embodiment according to the invention, the organic solvent is removed by evaporation by using a unit which allows a short residence time for the extraction solution in an evaporation stage. Therefore the organic solvent is particularly preferably separated from the extraction solution during evaporation by using a falling-film evaporator, thin layer evaporator and/or short-path evaporator or with the aid of this type of unit.

The expression "with the aid of this type of unit" is understood to mean, within the scope of the invention, that the unit mentioned with a short residence time for the extraction solution may also be combined with devices known to a person skilled in the art for separating solvents from extraction solutions. In this case, the units used to form the combination do not necessarily have to be those with a short residence time. At this point may be mentioned, inter alia, distillation columns which may be equipped for the introduction of steam or other suitable stripping agents, as required. Combinations which include several of the units with short residence times listed are also possible.

In an advantageous modification of the process according to the invention, the evaporation procedure is preferably operated in such a way that the smallest possible residual amount of solvent is produced. This is achieved, for example, by combining several of the units mentioned above with a stripping stage, which may be present as an additional unit or integrated into the previously mentioned units in the evaporation system such as, for instance, via direct introduction of the stripping medium into such an evaporator.

The specific conditions for evaporation necessarily vary with the particular solvent used for application in the extraction process. Basically, when using a separation unit with a short residence time for the evaporation process, it is preferred that the pressure during evaporation is not higher than 600 mbar, preferably 400 mbar and in particular 200 mbar.

The temperature to be used for evaporation generally depends on the solvent being separated. It is striven, however, and is thus also particularly preferred in the scope of the invention, to keep the temperature during evaporation no higher than 150° C. If this temperature is very clearly exceeded, then the desired product may be subject to thermal damage. Here, the temperature during evaporation is not necessarily understood to be the contact temperature of the product with the surface of the evaporation unit designed for short-term contact with the product. Rather, the temperature during evaporation is to be thought of as the average temperature in the evaporation unit. The temperature at the surface of the evaporation unit may, if necessary, be very much higher than 150° C. The brevity of contact time in the evaporation units used is the crucial factor. This avoids thermal damage, even if the contact temperature should be well above 150° C.

With regard to temperature distribution, it has proven in the scope of the invention that it is of special advantage for product quality if the temperature of the remaining extract directly at the outlet from the evaporation unit is between 30 and 100° C., preferably 50 to 95° C. and in particular 70 to 90° C.

As already mentioned, the residence time of the remaining extract is a crucial factor for the quality and composition of the MHA product striven for. In an advantageous development of the process according to the invention, the residence time of the remaining extract in the evaporation unit is not longer than 1.5 hours. This refers to the residence time in the whole evaporation system, which has at least one evaporation stage with a very short residence time. The residence time in the unit with a very short residence time is more likely to be within the minute range or less as against the maximum total residence time of 1.5 h cited. In this case, it is preferred in the scope of the invention, when evaporation consists of only a thin layer evaporator and/or a falling-film evaporator and/or a short-path evaporator, that the residence time in these units is not longer than 1 h, preferably 40 min.

In a further aspect, the process according to the invention also improves, in addition to the isolation procedure for MHA from the reaction mixture obtained by hydrolysis with sulphuric acid, the hydrolysis of MMP-CH itself. Thus, in a preferred embodiment according to the invention, hydrolysis of MMP-CH is performed in such a way that in a first stage the MMP-CH is hydrolysed with 60–85 wt. % strength, preferably 65–80 wt. % strength, sulphuric acid in the molar ratio of MMP-CH to $H_2SO_4$ of 1.0:0.5 to 1:1.05, preferably 1:0.6 to 1:0.8 at temperatures of 30–90° C., preferably 50–70° C., essentially with the production of MHA-amide. Here, essentially MHA-amide is produced from MMP-cyanohydrin, wherein the mixture being produced is essentially free of unconverted MMP-cyanohydrin. In other words, this means that the hydrolysis proceeds virtually quantitatively.

Furthermore, it is particularly advantageous to the invention if hydrolysis of the MHA-amide obtained in the first stage is carried out in a second stage by adding water and if necessary further sulphuric acid up to the stoichiometric upper limit, preferably however without the further addition of further $H_2SO_4$, at temperatures up to 140° C., preferably between 100 and 140° C., preferably under reflux conditions, in order to complete hydrolysis of the MHA-amide to give MHA. Basically, the second hydrolysis stage can also be performed at temperatures below 100° C., for example up to upper limits of temperatures of 90–100° C. In this case, however, the addition of further sulphuric acid up to a maximum of the stoichiometric upper limit, is required. In order to complete hydrolysis of the MHA-amide to give the desired MHA without adding further sulphuric acid, but only adding water, it has proven advantageous to the invention to use temperatures up to 140° C. It is also within the scope of the invention to perform the intermediate hydrolysis of MMP-cyanohydrin with, as compared with the prior art, more highly concentrated sulphuric acid in substoichiometric up to at most stoichiometric ratios, wherein in the case of substoichiometric addition in the first hydrolysis stage (amide formation) at lower temperature, to shorten the reaction time in the second stage, further sulphuric acid may optionally be added to reach the stoichiometric upper limit at elevated temperature, in order to complete conversion of the amide to the acid.

The invention also provides an improved MHA, which is obtainable by a process like the one described above. The improved MHA is characterised according to the invention in that it has more than 95 wt. % of total MHA where total MHA=the sum of monomeric MHA, MHA dimers and MHA oligomers and between more than 0.1 and less than 5 wt. % of water. In particular, it has proved advantageous to the invention that an MHA can be obtained, without a high degree of impairment in quality, which is characterised in that it has more than 98 wt. % of MHA as the sum of monomeric MHA, MHA dimers and MHA oligomers and a water content of between 0.1 and less than 2 wt. % and a kinematic viscosity of >100 mm$^2$/s at 25° C. Surprisingly, it has been demonstrated that the kinematic viscosity, measured by the Cannon-Fenske method, of the highly concentrated concentrate (that is MHA with at least 98 wt. % of active substance), after storage and dilution, is comparable with the kinematic viscosity of an 88 wt. % strength product. Despite a relatively high dimer and oligomer content of ca. 50 wt. % being set up in the concentrate after storage for ca. 300 days at room temperature, on dilution of the stored concentrate with water to ca. 88 wt. % its kinematic viscosity corresponds to that of the 88 wt. % strength commercial product which in corresponding storage tests has an equilibrium concentration of only ca. 25 wt. % of dimers and oligomers. In both cases, with both the diluted concentrate and the commercial product, the equilibrium state was reached. This fact is very surprising and is proven to be of great advantage for a variant of the MHA concentrate prepared according to the invention. In view of the fact that dimeric and oligomeric fractions generally impair the viscosity of the MHA which in practice is disadvantageous for practical processing, it was all the more surprising that, despite high initial contents in the so-called highly concentrated concentrate, an easily pumpable and thus transportable mixture with a convenient viscosity can be obtained. This has a number of advantages. In particular, the viscosity and above all the high active substance content mean that the concentrate can be transported more economically, since less water is transported, and yet nevertheless it can be diluted with water to standard concentrations in the food mill at the destination, without having to put up with unacceptably high viscosities.

Furthermore, it has turned out, within the scope of the invention, that an especially high quality MHA is obtainable following appropriate management of the hydrolysis reaction combined with the mild evaporation procedure used according to the invention with very short residence times. The MHA which can be particularly advantageously prepared is characterised in particular by a proportion of the sum of dimers and oligomers with respect to the total amount of MHA of ≦10 mol-%, preferably <7 mol-%. This means that, as compared with the prejudice. which is widespread in the prior art, a highly concentrated MHA is obtainable which represents a form which is very suitable for transport due to the extremely small proportion of dimers and oligomers. For an extended time of shipment, it may sometimes be necessary to convert the dimers and oligomers which are formed to an increasing extent, depending on the storage time, into monomer MHA again by the addition of water and the effect of elevated temperature.

Furthermore it is possible, within the scope of the invention, to use the highly concentrated MHA product to produce animal feedstuff supplements. In this case, it is shown that, by admixing the MHA concentrate with water, methionin and/or salts of MHA (preferably ammonium MHA) (optionally NH$_3$ to produce NH$_4$-MHA), all the nutritive values basically required by the market can be produced without any loss in quality.

Above all it has proved extremely surprising that, by performing the invention, the mixtures are obtainable not only by the addition of suitable mixing components such as water, methionin and/or ammonium MHA at the outlet for the desired MHA product from the evaporation stage, but that also and furthermore of particular advantage in the event that ammonium MHA is admixed, ammonia can be introduced directly into the MHA product from the evaporation stage. In this case, a desired proportion of the MHA is converted into ammonium MHA, depending on the amount of ammonia added.

Furthermore, it has proved to be particularly advantageous that a product based on the extraction solution which contains virtually no dimers or oligomers is obtainable if ammonia is added to the extraction solution before evaporation and the two phases produced are separated into an organic and an aqueous phase and the aqueous phase is fed to the evaporation unit which preferably-has a short residence time. With this method of operation, a mixture of MHA and ammonium MHA is produced at the outlet from the evaporation stage which contains virtually no dimers and oligomers. Furthermore, it is also possible to feed ammonia directly into the evaporation unit. In addition ammonia may also be used as a stripping medium.

In a particularly preferred embodiment according to the invention, the MHA obtainable by a process described herein, which contains more than 98 wt. % of MHA, calculated as the sum of monomeric MHA, MHA dimers and MHA oligomers, as well as more than 0.1 and less than 2 wt. % of water and having a kinematic viscosity of >100 mm$^2$/s at 25° C., is used to prepare mixtures for animal feedstuff supplements, wherein the use is characterised in that a mixture is prepared with methionin, whose MHA content including monomers, dimers and oligomers is <80 wt. % and whose oligomer content including MHA dimers and oligomers after storage for 300 days at room temperature is <25 mol. %, with respect to the total active substance content of MHA, dimers and oligomers and methionin.

The mixtures of MHA and methionin are animal feedstuff supplements with outstanding properties. With regard to methionin on its own, it is known that in practice it is barely soluble or even insoluble in all organic solvents (even in water). According to the invention, it was especially surprising that methionin dissolved well in MHA, even at room temperature. Furthermore, it is known from commercial 88 wt. % strength MHA, that an ca. 25 mol-% equilibrium concentration of dimers and oligomers is set up in 300 day storage tests at room temperature. As already mentioned above, the highly concentrated MHA has a much higher dimer and oligomer content of ca. 50 mol-% after a storage time of 300 days. When studying mixtures of methionin and MHA in the storage tests, it has been shown, surprisingly, that after 300 days storage time, in an advantageous manner, a significantly smaller proportion of oligomers and dimers is present. This is, for example, 20 mol-% after 300 days, wherein this still has to be corrected for the methionin substitution for MHA, which leads to a change in the value to ca. 21.5 mol-%. Nevertheless, this improvement is significant because a lower oligomer content is required due to the less favourable biological efficacy of the monomers. Even an improvement of "only" 3.5 mol-% can lead to a significant improvement in the efficacy of the product in animal feedstuff supplements. In particular, the tendency towards improved activity is crucial. In addition, the cold storage stability of mixtures of MHA and methionin, surprisingly, is greatly improved. A mixture of 78 wt. % of MHA and 10 wt. % of methionin at −20° C. shows no tendency whatsoever to crystallise after 4 weeks (thus no substance precipitates out), which is surprising because methionin in other solvents under comparable conditions, precipitates immediately. Current market products with ca. 88 wt. % of MHA content begin to precipitate at −20° C. after 3 to 21 days. Thus, in an advantageous manner, the mixtures of methionin and MHA do not require the use of supplementary heating to a certain extent when being transported for prolonged periods under cold conditions. Also storage under corresponding cold conditions is considerably simpler because costly additional heating is not required. In addition it is noteworthy that MHA enhances the methionin additive with regard to biological efficacy. This is novel and surprising because to date no methionin-containing MHA liquid formulations have been disclosed and the availability of such mixtures would not have been immediately obvious to a person skilled in the art, due to the unexpected solubility of methionin in MHA. In particular, a mixture of MHA and methionin is the first liquid feedstuff supplement with a biological efficacy which is greater than that of the only known liquid feedstuff additives based on MHA.

In yet another preferred embodiment, the invention provides the use of MHA as it is obtainable from a process as described above, for preparing mixtures for animal feedstuff supplements, wherein the use is characterised in that a mixture is prepared using gaseous ammonia, aqueous ammonia and/or ammonium MHA, whose MHA content, including monomer, dimers and oligomers is <80 wt. % and whose oligomer content including MHA dimers and oligomers, after storage for 30 days at 40° C., is <25 mol-%, with respect to the total active substance content of MHA, dimers, and oligomers. With regard to storage-stability at room temperature or during cold storage, mixtures of MHA and ammonium MHA also demonstrate astonishing advantages as compared with pure MHA, wherein these advantages, like those of mixtures of MHA and methionin, could not have been easily foreseen. In particular, ammonia has an advantageous effect on the position of the equilibrium between monomers, dimers and oligomers.

BRIEF DESCRIPTION OF THE DRAWINGS

The invention is explained in more detail in the following by making use of examples which refer to the enclosed figure.

The figures show.

EXAMPLES

Analytical methods of determination and definitions

The concentrations of MMP-cyanohydrin, MHA-amide, MHA monomers and methionin were quantitatively determined in the process solution by HPLC by means of comparison with an external standard (pure substance).

The concentration of total MHA=(tot. MHA)=MHA-amide (optional)+MHA monomer+MHA (dimers+ oligomers)+methionin (optional)

was determined by titrimetric determination of the thio-ether function using a $KBr/KBro_3$ standard solution and expressed as the sum of the corresponding MHA monomer equivalents in [wt. %] or [g] or [mol] or [mol-%].

The concentration of MHA dimers+MHA oligomers (DIM+OLI) was determined by calculating the difference between total MHA and MHA monomer+(optional MHA-amide and/or methionin) and expressed as the sum of the corresponding MHA monomer equivalents in [wt. %] or [g] or [mol] or [mol-%].

The water content was determined by Karl-Fischer titration, the MIBK content by GC or a difference sum, the sulphate or ammonium content by ionic chromatography using standard methods.

Example 1

In a set of experiments, it was investigated to what extent MMP-cyanohydrin is converted into MHA-amide on contact with aqueous sulphuric acid under various conditions.

Performing Experiment 1

141g (1.03 mol) of 65% $H_2SO_4$ at 50° C. were initially placed in a 1 l three-necked flask with a reflux condenser, dropping funnel, internal thermometer and magnetic stirrer and 138 g (1.0 mol) of 95% MMP-cyanohydrin were added dropwise over 30 minutes with stirring. After a further 15 min post reaction time at this temperature, MMP-cyanohydrin could no longer be detected in the reaction solution.

Performing Experiment 2

Experiment 2 was performed in the same way as experiment 1 using 72 g (0.55 mol) of 75% $H_2SO_4$ and 138 g (1.0 mol) of 95% MMP-cyanohydrin. After 150 min post reaction time, 0.1% of the theoretical amount of MMP-cyanohydrin could still be detected.

Performing Experiment 3

155 g (1.03 mol) of 65% $H_2SO_4$ and 138 g (1.0 mol) of 95% MMP-cyanohydrin were simultaneously supplied over 15 minutes at a temperature of 50° C. to a 1 l four-necked flask with a reflux condenser, two dropping funnels, an internal thermometer and a magnetic stirrer. After a further 15 min post reaction time at this temperature, MMP-cyanohydrin could no longer be detected.

Performing Experiments 4–11

Experiments 4–11 were performed in the same way as experiment 3 with the reaction parameters and results summarised in Table 1.

TABLE 1

Reaction conditions

| Expt. No. | Molar ratio MMP-CH:H$_2$SO$_4$ | H$_2$SO$_4$ conc. [wt. %] | Reaction temp. [° C.] | Reaction time [min] to 0% MMP-CH | Reaction time [min] to > 0.3% MMP-CH | Feed time for MMP-CH[1]) and H$_2$SO$_4$[2]) [min] | Post reaction time final sample | Residual MMP-CH in mol-% |
|---|---|---|---|---|---|---|---|---|
| 1  | 1:1.03 | 65   | 50    | <15     | —       | 30[1]) | 30  | 0    |
| 2  | 1:0.55 | 75   | 50    | >150    | ~60     | 30[1]) | 150 | 0.1  |
| 3  | 1:1.03 | 65   | 50    | <15     | —       | 15[2]) | 15  | 0    |
| 4  | 1:0.55 | 75   | 50    | >75     | ~60     | 15[2]) | 75  | 0.15 |
| 5  | 1:0.55 | 75   | 90    | >105    | ~15     | 15[2]) | 105 | 0.07 |
| 6  | 1:1.03 | 65   | 90    | 0       | —       | 15[2]) | 15  | 0    |
| 7  | 1:0.55 | 75   | 50–90 | ~20–30  | ~10–15  | 15[2]) | 30  | 0    |
| 8  | 1:0.6  | 75   | 50    | >75     | ~30–40  | 15[2]) | 75  | 0.05 |
| 9  | 1:0.65 | 76.4 | 50    | >45     | ~15     | 15[2]) | 45  | 0.14 |
| 10 | 1:0.7  | 78.9 | 50    | 5–10    | <5      | 15[2]) | 15  | 0    |
| 11 | 1:1.03 | 75   | 50    | 0       | 0       | 15[2]) | 15  | 0    |

As shown in Table 1, complete conversion of MMP-CH was found within the stated reaction times in experiments 1, 3, 6, 7, 10 and 11.

The reaction time required for complete conversion of MMP-CH with H$_2$SO$_4$ increases with increasing molar ratio of MMP-CH to H$_2$SO$_4$ (compare experiments 8 and 11). The different sequences of addition of the substances used which was practised here ([1]) or [2])) had no serious effect on the reaction results (compare experiments 1 and 3 or 2 and 4).

Example 2

Performing experiment 1

35.8 g (0.35 mol, 0.7 mol equ.) of 96% H$_2$SO$_4$ in a 500 ml three-necked flask with a reflux condenser, dropping funnel, internal thermometer and magnetic stirrer were diluted with water to a sulphuric acid concentration of 78.9 wt. % H$_2$SO$_4$. Over the course of 23 minutes, with stirring, 67.5 g (0.5 mol) of 97.2% MMP-CH were added dropwise at a temperature of 49–56° C. After a further 20 min post reaction time at ca. 50° C., complete conversion of cyanohydrin (0 wt. %) to MHA-amide (66.2 wt. %) was confirmed by means of HPLC analysis. The contents of the flask were transferred by means of 42.3 g of water to a 200 ml steel autoclave with a glass insert, internal temperature measuring device, manometer and magnetic stirrer so that the concentration of the aqueous sulphuric acid present in the reaction mixture was 44 wt. %.

After sealing the autoclave, the reaction mixture was taken to a reaction temperature of 140° C. over the course of 45 min and stirred at this temperature for another 120 min. After cooling and opening the autoclave, 150.4 g of MHA hydrolysate were obtained. A total amount of 71.5 g (0.48 mol, 95.2% of theoretical yield) of MHA were obtained, as measured by titration of the sulphuric acid equivalents with bromide/bromate solution. 57.5 g (76.6% of theoretical) of MHA monomer were found by means of HPLC analysis. By difference, this gives 14.0 g (18.6% of theoretical) of MHA (dimers+oligomers), each expressed as MHA monomer. MHA-amide could no longer be detected by means of HPLC.

Performing Experiments 2–5

Experiments 2–5 were performed in the same way as experiment 1, with the reaction parameters and results summarised in Table 2. In experiment 4, the 1st stage was performed in a 2 l glass flask, the 2nd stage in a 2 l autoclave, in experiment 5 both stages were performed in a 2 l glass flask.

TABLE 2

1st stage: MHA-amide formation

| | Reaction conditions | | | | | Results | | |
|---|---|---|---|---|---|---|---|---|
| Expt. No. | 97.2% MMP-CH [g] [mol] | 96% H$_2$SO$_4$ [g] | H$_2$SO$_4$ [mol equ.] | Aqu. H$_2$SO$_4$ [wt. %] | Temp. [° C.] | Time for .addition .reaction [min] | Conc. of MHA-amide [wt. %] | Conc. of MMP-CH [wt. %] |
| 1 | 67.5 0.5 mol | 35.8  | 0.7  | 78.9 | 49–56 | 23 20 | 66.2 | 0 |
| 2 | 67.5 0.5 mol | 35.8  | 0.7  | 78.9 | 49–56 | 23 20 | 66.2 | 0 |
| 3 | 67.6 0.5 mol | 28.1  | 0.55 | 75   | 46–56 | 35 20 | 67.8 | 0 |
| 4 | 404 3.0 mol  | 168.6 | 0.55 | 75   | 45–90 | 35 30 | n.d. | n.d. |
| 5 | 269.7 2.0 mol | 204.1 | 1.0 | 65   | 50    | 60 30 | 43.6 + 6.4 MHA | 0 |

TABLE 2-continued

2nd stage: MHA hydrolysate formation

| | Reaction conditions | | | Results [% of th.] | | | |
|---|---|---|---|---|---|---|---|
| Expt. No. | Aqu. $H_2SO_4$ [wt. %] | Temp. [° C.] | Time [min] | MHA-amide[1] | Total MHA[2] | MHA-mono[1] | MHA dimers + oligomers[3] |
| 1 | 44 | 56–140 140 | 45 120 | 0 | 95.2 | 76.6 | 18.6 |
| 2 | 44 | 56–140 140 | 65 60 | 0 | 97.5 | 78.6 | 18.9 |
| 3 | 44 | 56–140 140 | 35 120 | 3.8 | 99.1 | 76.4 | 18.9 |
| 4 | 24.3 | 50–100 100 100–140 140 | 18 60 57 90 | 1.4 | 95.0 | 88.1 | 5.5 |
| 5 | 43 | 50–90 90 | 15 120 | 0.2 | 99.6 | 90.1 | 9.3 |

[1]HPLC
[2]Bromide/bromate titration
[3]Difference calculated from 1) and 2)
n.d. = not determined

Example 3

Isolating highly concentrated MHA from MRA hydrolysate by means of liquid/liquid extraction and evaporating the extraction solution.

Figure 1:
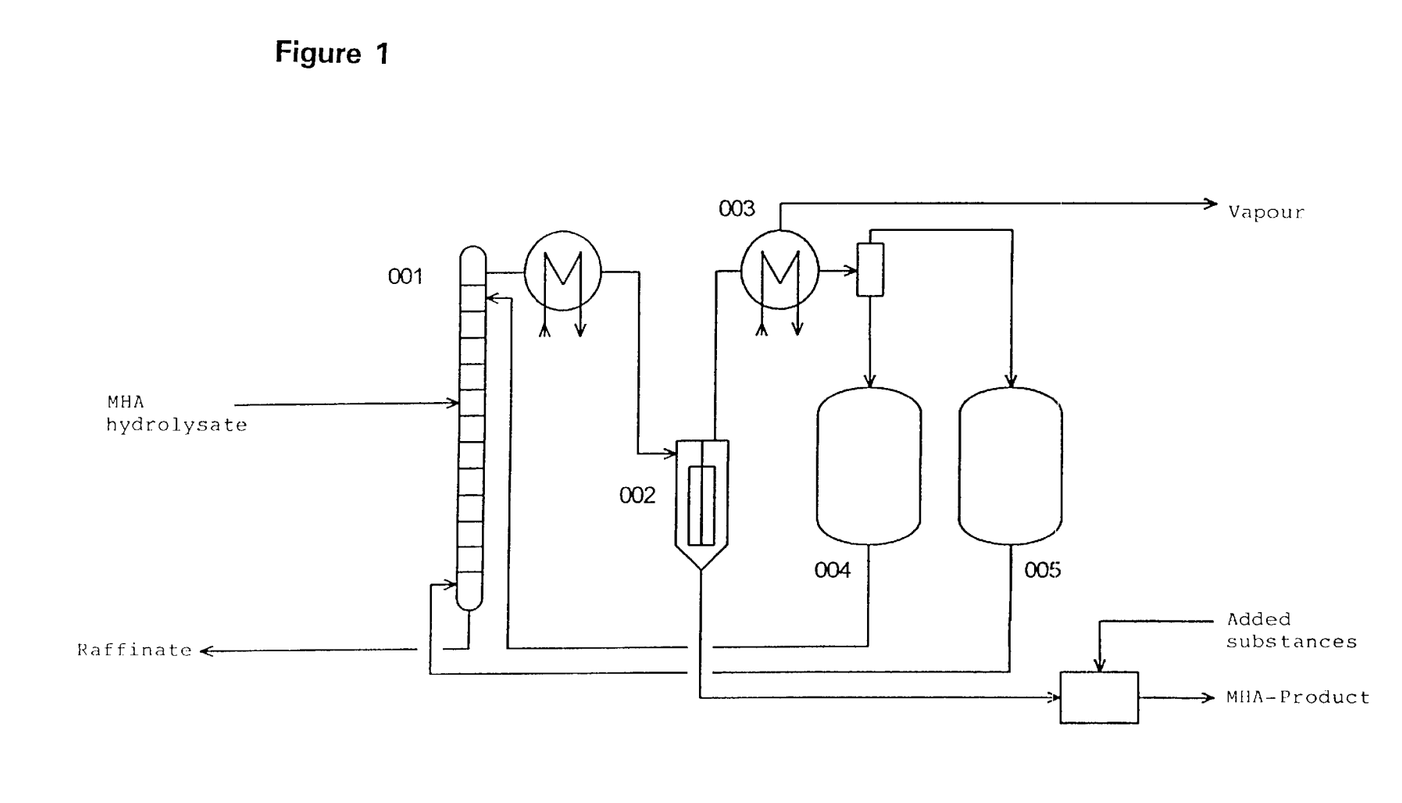
FIG. 1 a schematic overview of part of a large-scale plant for recovering MHA, wherein for simplicity only the working-up section is shown.

Process description making reference to FIG. 1

FIG. 1 shows a schematic diagram of the apparatus used for example 3. This comprises essentially the following apparatus Extraction column (001)=pulsed perforated plate column, 3 m long, 2.1 cm internal diameter, 60 perforated plates, heated double-walled jacket Thin layer evaporator (002)=Sambay evaporator with 0.08 $m^2$ exchange area, heated double-walled jacket Condensation system (003)=water-cooled glass condenser Collection containers for recycled water and solvent (004/005)

The MHA hydrolysate leaving the MHA hydrolysis stage which consists essentially of MHA (monomer+dimers+oligomers+optional amide), $(NH_4)_2SO_4$ and/or $NH_4HSO_4$ and water, is fed to a level above the 40th plate in extraction column 001, after being preheated to the extraction temperature. The solvent (here methylisobutyl ketone=MIBK), also preheated, is pumped in at the bottom of the column (countercurrent principle). In addition, the head of the column is supplied with wash water. The raffinate, containing essentially $(NH_4)_2SO_4$ and/or $NH_4HSO_4$ and water, is withdrawn at the bottom of the column. The extraction solution containing essentially MHA, solvent and water is abstracted at the head of the column and then fed to the Sambay evaporator 002. There, MIBK and $H_2O$ are removed together from the extraction solution by applying a vacuum and blowing in additional $H_2O$ vapour, as well as a current of $N_2$ just in front of the outlet from the evaporator. The evaporation process was operated in such a way that <2 wt. % of $H_2O$ could be detected at the Sambay outlet (Karl Fischer titration) and the highly concentrated MHA being discharged was virtually solvent-free.

The solvent/water mixture emerging from evaporator 002 was first condensed in 003 and then taken to a separation vessel for separation. Solvent and water were each collected in a collection container, 004 and 005 respectively, and from there returned to the extraction system. The Sambay discharge, cooled to room temperature, was taken to a product collection container.

The conditions and results of the individual experiments 1–4 are tabulated in the following summary.

The composition of the extraction solution was analysed immediately after leaving the head and the composition of the raffinate solution was analysed immediately after leaving the bottom of extraction column 001.

The composition of the highly concentrated MHA was determined in the Sambay discharge directly after leaving the discharge point.

The MHA hydrolysate solutions used for extraction were prepared in a pressure-stabilised 400 l stirred tank from 114.7 kg (874 mol) of MMP-cyanohydrin and 85.7 kg (874 mol, 1.00 mol equ.) of $H_2SO_4$ under the conditions given in example 2, experiment S or from 142.9 kg (1089 mol) of MMP-cyanohydrin and 110.0 kg (1122 mol, 1.03 mol equ.) of $H_2SO_4$ under the conditions in example 2, experiment 5 or from 115.3 kg (879 mol) of MMP-cyanohydrin and 47.5 kg (484 mol, 0.55 mol equ.) of $H_2SO_4$ under the conditions in example 2, experiment 4. Optionally present highly volatile secondary products were removed from the crude hydrolysate solutions by applying a vacuum after the end of each reaction and the solutions were then analysed. The compositions of the MHA hydrolysates thus obtained and which were used for extraction are given for each of the individual experiments in example 3.

Preparation of highly concentrated MHA

Experiment 1

Feedstock of MHA hydrolysate from MMP-cyanohydrin and 1.0 mol equ. of $H_2SO_4$.

Feedstock used for extraction:

| Mass flows | MIBK | 5 kg/h |
|---|---|---|
| | MHA hydrolysate | 8.4 kg/h |
| | total MHA | 3.4 kg/h |
| | wash $H_2O$ | 0.5 kg/h |
| | MIBK/hydrolysate | 0.6 [–] |

Composition of the MHA hydrolysate:
(prepared in the same way as in example 2, experiment 5)
tot. MHA: 42 wt. %; MHA 90 mol-%; dimers+oligomers 10 mol-%
$H_2O$: 28.9 wt. %
$SO_4^{2-}$: 25.9 wt. %
Extraction (001):

Temperature: 60° C. (average)
Compositions

| of the extraction solution: | MIBK | 47 wt. % |
|---|---|---|
| | tot. MHA | 40 wt. % |
| | $H_2O$ | 13 wt. % | of the raffinate: tot. MHA 0.1 wt. %
Evaporation (002):
Pressure: 100 mbar
Sambay
    temperature in the heating jacket: 150° C.
        at the head: 62° C.
        at the bottom: n.d.
    stripping steam: 0.5 kg/h
    $N_2$ stripping gas 100 l/h
    composition of highly concentrated MHA at bottom discharge: tot. MHA 98 wt. %; MHA 86 mol-% dimers+oligomers 14 mol-%
    $H_2O$: 2 wt. %
    MIBK: 40 ppm
About 3.5 kg/h of MHA concentrate with the composition given above were obtained at the bottom Sambay discharge point.

Experiment 2
Feedstock of MHA hydrolysate from MMP-cyanohydrin and 1.03 mol equ. of $H_2SO_4$.
Feedstock used for extraction:

| Mass flows | MIBW | 3.6 kg/h |
|---|---|---|
| | MHA hydrolysate | 5.38 kg/h |
| | total MHA | 2.10 kg/h |
| | wash $H_2O$ | 0.5 kg/h |
| | MIBK/hydrolysate | 0.67 [–] |

Composition of the MHA hydrolysate:
(prepared in the same way as in example 2, experiment 5)
tot. MHA: 39.0 wt. %; MHA 86.9 mol-t; dimers+oligomers 13.1 mol-%
$H_2O$: ca. 30 wt. % (residue)
$SO_4^{2-}$: 25.4 wt. %
$NH_4HSO_4$: 30.4 wt. %
Extraction (001):
Temperature: 54° C. (average)
Compositions
of the extraction solution: MIBK ≦54 wt. %
    tot. MHA 34.1 wt. %
    $H_2O$ 11.9 wt. %
of the raffinate: tot. MHA 0.3 wt. %
    $SO_4^{2-}$ 30.4 wt. %
    MIBK 0.17 wt. %
Evaporation (002):
Pressure: 100 mbar
Sambay
    temperature in the heating jacket: 150° C.
        at the head: 65° C.
        at the bottom: 92° C.
    stripping steam: 0.7 kg/h
    $N_2$ stripping gas 100 l/h
    composition of highly concentrated MHA at bottom discharge: tot. MHA 99.2 wt. %; MHA 86.9 mol-% dimers+oligomers 13.1 mol-%
    $H_2O$: 0.8 wt. %
    $SO_4^{2-}$: 0.43 wt. %
    MIBK: 28 ppm
About 2.1 kg/h of MHA concentrate with the composition given above were obtained at the bottom Sambay discharge point.

Experiment 3
Feedstock of MHA hydrolysate from MP-cyanohydrin and 0.55 mol equ. of $H_2SO_4$.
Feedstock used for extraction:

| Mass flows | MIBK | 3.6 kg/h |
|---|---|---|
| | MHA hydrolysate | 6.55 kg/h |
| | total MHA | 2.62 kg/h |
| | wash $H_2O$ | 0.5 kg/h |
| | MIBK/hydrolysate | 0.55 [–] |

Composition of the MHA hydrolysate:
(prepared in the same way as in example 2, experiment 4)
tot. MHA: 40 wt. %; MHA 94.7 mol-%; dimers+oligomers 5.3 mol-%
$H_2O$: ca. 40.2 wt. %
$SO_4^{2-}$: 13.9 wt. %
$NH_4^+$: 4.85 wt. %
Extraction (001):
Temperature: 52° C. (average)
Compositions
of the extraction solution: MIBK ~49 wt. %
    tot. MHA 35.8 wt. %
    $H_2O$ 14.9 wt. %
of the raffinate: tot. MHA 0.13 wt. %
Evaporation (002):
Pressure: 100 mbar
Sambay
    temperature in the heating jacket: 150° C.
        at the head: 59° C.
        at the bottom: 92° C.
    stripping steam: 0.6 kg/h
    $N_2$ stripping gas 100 l/h
    composition of highly concentrated MHA at bottom discharge: tot. MHA 98.8 wt. %; MHA 95.1 mol-% dimers+oligomers 4.9 mol-%
    $H_2O$: 0.5 wt. %
    $SO_4^{2-}$: 0.18 wt. %
    MIBK: 477 ppm
About 2.7 kg/h of MHA concentrate with the composition given above were obtained at the bottom Sambay discharge point.

Experiment 4
Feedstock of MHA hydrolysate from MMP-cyanohydrin and 0.55 mol equ. of $H_2SO_4$.
Feedstock used for extraction:

| Mass flows | MIBK | 3.6 kg/h |
|---|---|---|
| | MHA hydrolysate | 6.89 kg/h |
| | total MHA | 2.76 kg/h |
| | $H_2O$ | 0.5 kg/h |
| | MIBK/hydrolysate | 0.52 [–] |

Composition of the MHA hydrolysate:
(prepared in the same way as in example 2, experiment 4)
tot. MHA: 40 wt. %; MHA 94.7 mol-%; dimers+oligomers 5.3 mol-%
$H_2O$: 40.2 wt. %
$SO_4^{2-}$: 13.9 wt. %
$NH_4^+$: 4.85 wt. %

Extraction (001):

Temperature: 52° C. (average)

Compositions of the extraction solution: MIBK ca. 49.3 wt. % tot. MHA 35.8 wt. %

$H_2O$ 14.9 wt. % of the raffinate: tot. MHA 0.1 wt. %

Evaporation (002):

Pressure: 100 mbar

Sambay temperature in the heating jacket: 150° C.

at the head: 59° C.

at the bottom: 95° C.

stripping steam: 0.6 kg/h

$N_2$ stripping gas 100 l/h composition of highly concentrated MHA at bottom discharge: tot. MHA: 99 wt. %; MHA 94.9 mol-% dimers+oligomers 5.1 mol-%

$H_2O$: 0.2 wt. %

$SO_4^{2-}$: 0.16 wt. %

MIBK: 482 ppm

About 2.8 kg/h of MHA concentrate with the composition given above were obtained at the bottom Sambay discharge point.

As a comparison of experiments 1–4 shows, an MHA concentrate with $\geq 98$ wt. % of total MHA and 0.2 to 2 wt. % of water can be obtained without any product damage occurring [enlarged MHA-(dimers+oligomers) fraction]. This surprising result is shown in a particular way in the MHA concentrates from the low-sulphate MHA hydrolysis solutions (experiments 3 and 4). Here, the MHA-(dimers+ oligomers) fraction is only 4.9–5.1 mol-%, as compared with 13.1–14 mol-% in experiments 1 and 2. The ratio of the proportion by weight of MHA monomers to the sum of dimers+oligomers [=MHA/MHA-(dim+oli)] is about 19 and 6.1–6.6 respectively. In all the cases shown here, the MHA-(dimers+oligomers) fraction is thus well under the conventional values for MHA commercial products which have an MHA-(dimers+oligomers) fraction of about 20–25 mol-%.

In addition, it has been possible crucially to improve the ratio of the MHA/MHA-(dim+oli) proportion by weight as compared with the values given in examples 1–6 of patent EP 0 142 488, these being 3.3; 3.2; 3.7 (example 1), 1.8 (example 2), 3.0 (example 3), 5.4 (example 5) and 5.2 (example 6).

Example 4

Preparation of a MHA-methionin-$H_2O$ mixed product from MHA concentrate

Experiment 1

Experiment 1 was performed in the same way as example 3, experiment 2 with the difference that the methionin and water were added to the discharge from the bottom of the Sambay evaporator in a stirred tank and a homogeneous solution with 89 wt. % of total MHA*) and ca. 10 wt. % of water was produced by stirring. For this, 3.2 kg of D, L-methionin (=Met) and 3.2 kg of water were added to a total of 25.7 kg of the MHA concentrate with the composition mentioned, and the mixture was homogenised by stirring. The product produced in this way (32.1 kg) had the following analytically determined composition:

| | |
|---|---|
| total MHA*) | 89.2 wt. % ≈ 100.0 mol-% |
| MHA monomer | 64.8 wt. % ≈ 72.6 mol-% |
| MHA (dimer + oligomer) | 15.1 wt. % ≈ 16.7 mol-% |
| Met | 9.2 wt. % ≈ 10.7 mol-% |
| $SO_4^{2-}$ | 0.8 wt. % |
| MIBK | 14 ppm |

*)here total MHA ≈ MHA-(monomer + dimer + oligomers) + Met

Experiment 2

Experiment 2 was performed in the same way as example 3, experiment 3 with the difference that the methionin and water were added to the discharge from the bottom of the Sambay evaporator in a stirred tank and a homogeneous solution with 88 wt. % of total MHA*) and ca. 11 wt. % of water was produced by stirring. For this, 3.5 kg of D, L-methionin and 4.0 kg of water were added to a total of 27.0 kg of the MHA concentrate with the composition mentioned, and dissolved by stirring. The product produced in this way (34.5 kg) had the following analytically determined composition:

| | |
|---|---|
| total MHA*) | 88.1 wt. % ≈ 100.0 mol-% |
| MHA monomer | 73.8 wt. % ≈ 83.8 mol-% |
| MHA (dimer + oligomer) | 4.3 wt. % ≈ 4.9 mol-% |
| Met | 10.0 wt. % ≈ 11.4 mol-% |
| $SO_4^{2-}$ | 0.16 wt. % |
| MIBK | 482 ppm |

*)here total MHA = MHA-(monomer + dimer + oligomers) + Met

Example 5

Preparation of MHA-$NH_4$ salt solution from MHA concentrate 98.3 g of MHA extraction solution with a concentration of 40 wt. % (0.26 mol) of total MHA, 13 wt. % of water and ca. 47 wt. % of MIBK, prepared as in example 3, experiment 1, was evaporated for 2.4 hours at 55–70° C. under a water-jet vacuum. 17.7 g (0.26 mol) of 25% aqueous ammonia solution was added to the residue (total MHA of 99.9 wt. %). This caused the temperature to increase to 53° C. After cooling to room temperature, 57.6 g of a brown, clear liquid with the following composition was obtained:

| | |
|---|---|
| total MHA | 68.3 wt. % |
| MHA monomer | 59.5 wt. % |
| MHA-amide | 0.0 wt. % |
| MHA-(dimers + oligomers) | 8.8 wt. % |
| $NH_4^+$ | 8.1 wt. % |
| $H_2O$ | 22.4 wt. % |

Example 6

Preparation of a MHA-NH4 salt solution from MHA extraction solution 3502 g of MHA extraction solution with a concentration of 35.8 wt. % of total MHA, 14.9 wt. % of $H_2O$ and ca. 49 wt. % of MIBK, prepared as in example 3, experiment 4, was cooled to 5° C. in an ice bath. Into this solution was passed 300 g (17.6 mol) of gaseous ammonia at a temperature of 5–21° C. over the course of 3.5 h. Two liquid phases formed. The heavier phase (2202 g) was isolated and residual MIBK was removed by the passage of water vapour at 60° C. and 100 mbar pressure. The residue was concentrated at 50° C. (2 h) under a water jet vacuum, wherein an oily brown-yellow liquid (1583 g) with the following composition was obtained:

| total MHA | | 81.2 wt. % (≈103% of theoretical) |
|---|---|---|
| incl: | MHA monomer | 79.3 wt. % |
| | MHA-amide | 1.9 wt. % |
| | MHA-(dimers + oligomers) | 0.0 wt. % |
| $MH_4^+$ | | 9.0 wt. % |
| water | | 9.8 wt. % |

After dilution with 230 g of water and 20 g of 25% strength ammonia solution, a very mobile pale brown liquid (1743 g) with the following composition was obtained:

| total MHA | | 70.0 wt. % |
|---|---|---|
| incl: | MHA monomer | 68.3 wt. % |
| | MHA-amide | 1.7 wt. % |
| | MHA-(dimers + oligomers) | 0.0 wt. % |
| $NH_4^+$ | | 8.1 wt. % |
| $H_2O$ | | 20.0 wt. % |

Surprisingly, unwanted MHA-(dimers+oligomers) could no longer be detected in the product solution after this treatment. Only a negligible amount of MHA-amide was formed as the single secondary product.

Example 7

Preparation of an MHA-MHANH$_4$—H$_2$O mixed product from MHA extraction solution
Experiment 1

Using the conditions essentially given in example 3, experiment 2, 10 kg of MHA extraction solution with a concentration of 39.7 wt. % of total MHA, ca. 12 wt. % of H$_2$O and ca. 48 wt. % of MIBK were evaporated in the Sambay evaporator. The solution being discharged was diluted with altogether 0.636 kg (3.06 mol) of an 8.2% strength aqueous NH$_3$ solution and thoroughly mixed.

An oily, brown-yellow liquid (4.60 kg) with the following composition was thereby obtained (pH ~2.3):

| Total MHA | | 86.2 wt. % (≈100% of th.) |
|---|---|---|
| incl: | MHA monomer | 74.3 wt. % |
| | MHA-amide | 0.0 wt. % |
| | MHA (dimers + oligomers) | 11.9 wt. % |
| $NH_4^+$ | | 1.2 wt. % |
| $SO_4^{2-}$ | | 0.22 wt. % |
| $H_2O$ | | 13.5 wt. % |
| MHANH$_4$* | | 10.75 wt. % |

*Calculated value for proportion of MHA-NH$_4$ proportion (≈11.2 mol-% as monomer, dimers and oligomers)

Experiment 2

Using the conditions essentially given in example 3, experiment 2, 10 kg of MHA extraction solution with a concentration of 35.1 wt. % of total MHA, ca. 12.7 wt. % of H$_2$O and ca. 52 wt. % of MIBK were evaporated in the Sambay evaporator. The solution being discharged was diluted with altogether 0.45 kg (4.23 mol) of a 16.0% strength aqueous NH$_3$ solution and thoroughly mixed.

An oily, brown-yellow liquid (3.96 kg) with a pH of ca. 2.7 and with the following composition was thereby obtained:

| Total MHA | | 88.6 wt. % (≈100% of th.) |
|---|---|---|
| incl: | MHA monomer | 76.9 wt. % |
| | MHA-amide | 0.0 wt. % |
| | MHA (dimers + oligomers) | 11.7 wt. % |
| $NH_4^+$ | | 1.94 wt. % |
| $SO_4^{2-}$ | | 0.15 wt. % |
| $H_2O$ | | 9.8 wt. % |
| MHANH$_4$* | | 17.70 wt. % |

*Calculated value for proportion of MHA-NH$_4$ proportion (≈17.7 mol-% as monomer, dimers and oligomers)

Example 8

Figure 2:
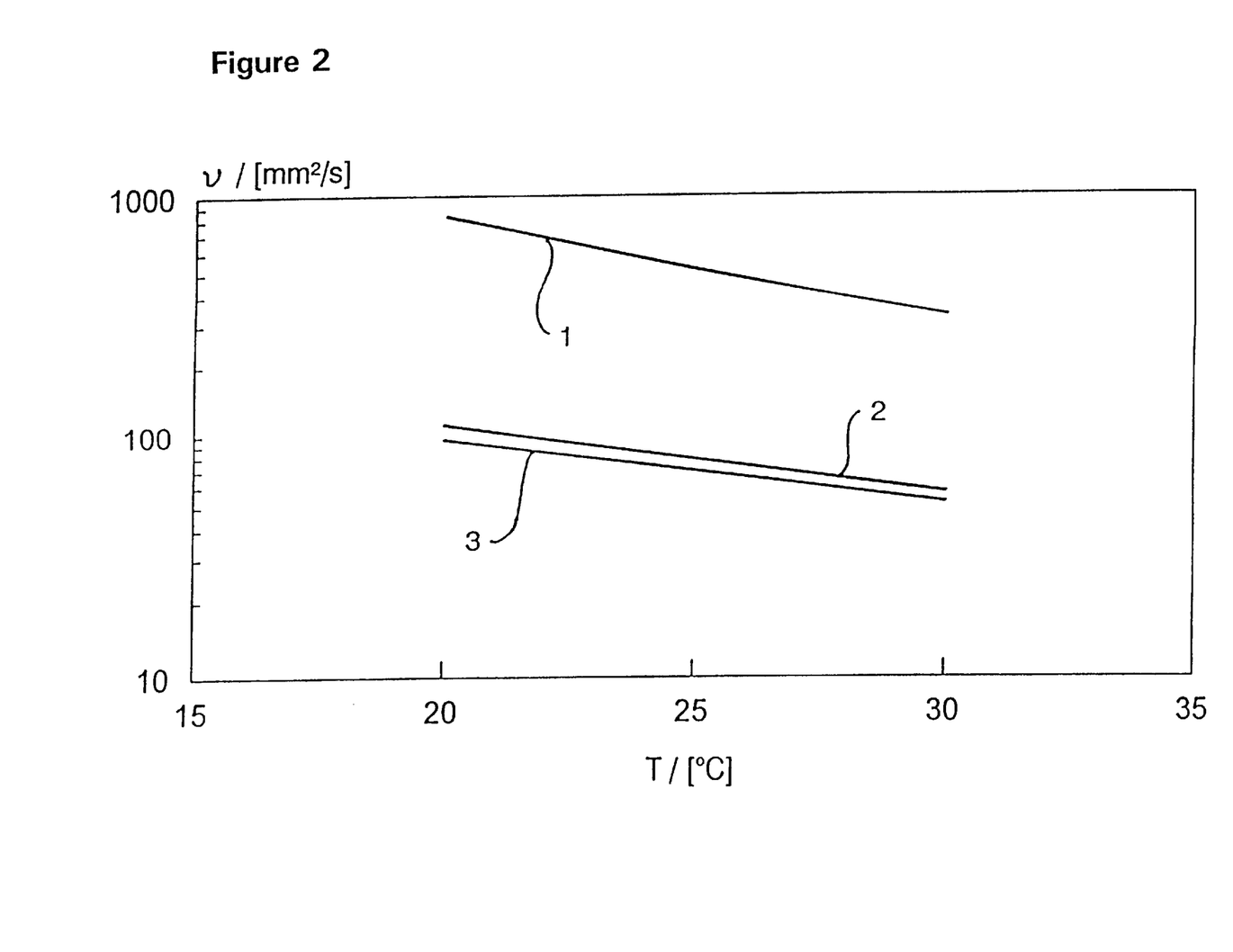
FIG. 2 a plot of the Canon-Fenske kinematic viscosity for highly concentrated MHA (ca. 98 wt. %) stored for 300 days, as compared with an 88 wt. % commercial product, as well as an MHA solution adjusted to 88 wt. % MHA by using water to dilute a concentrate which has been stored, at different temperatures.

Determining the Cannon Fenske viscosity:

The variation in kinematic viscosities with temperature was determined, as can best be seen in FIG. 2, with an opaque Canon-Fenske viscometer using the ISO 3105-1976 method, for the following MHA qualities:

98% MHA, prepared as in example 3, experiment 2 and stored at room temperature for >300 days, corresponding to the curve with the reference number 1 in FIG. 2, 88% MHA from 98% MHA, prepared as in example 3, experiment 2, stored at room temperature for >300 days and then diluted to 88%, corresponding to the curve with the reference number 2 in FIG. 2, and 88 W MHA as a commercial product, corresponding to the curve with the reference number 3 in FIG. 2.

Despite the relatively high dimer and oligomer content directly after dilution with water, the viscosity of the MHA 88 produced from 98 (2) corresponded to that of the commercially produced MHA 88 (3).

Example 9

Storage experiments using MHA products

Figure 3:
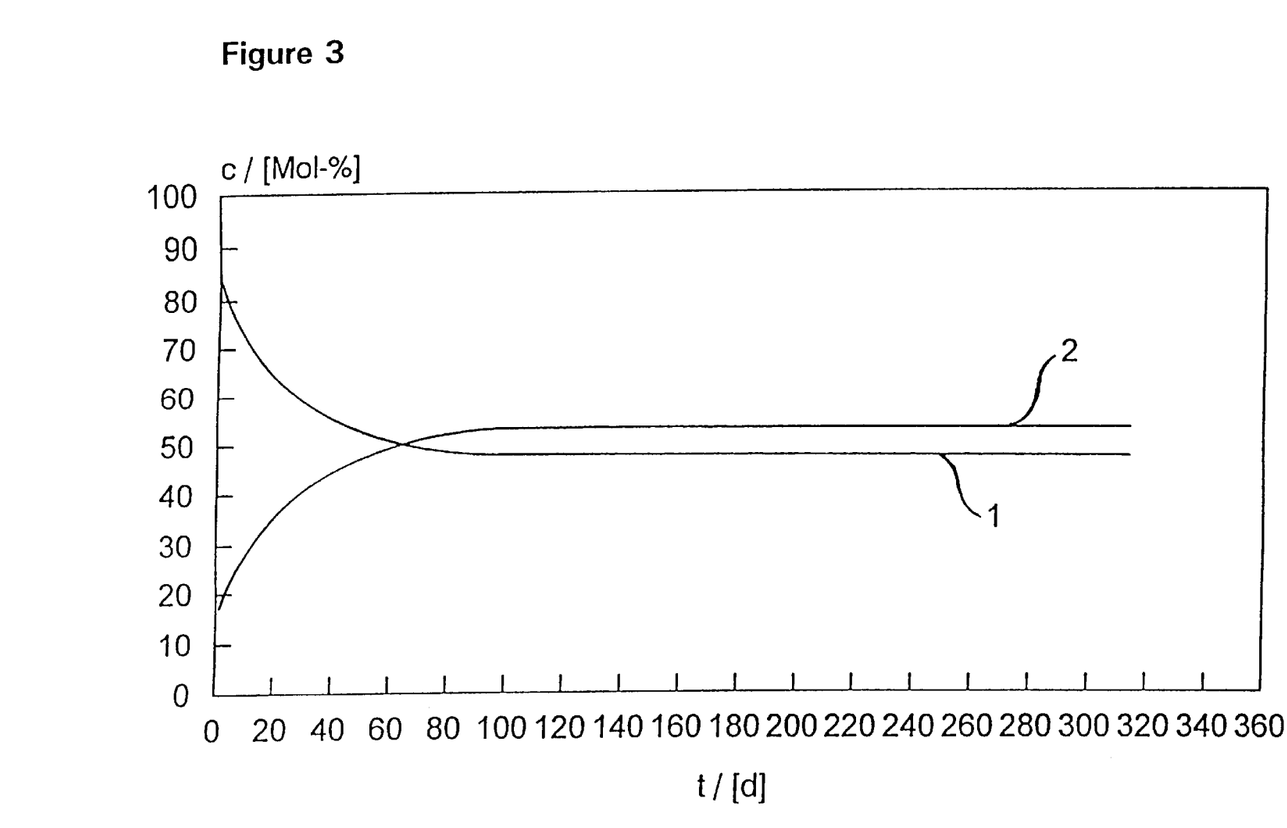
FIG. 3 a representation of the variation in concentration of MHA and dimers+oligomers during the storage of MHA concentrate (ca. 98 wt. %) for 300 days at room temperature.

The products mentioned in FIGS. 3 to 6 were each stored in a sealed glass vessel without stirring, at the temperatures quoted for a period of up to 310 days. At regular intervals, samples were withdrawn and the concentration of total MHA, MHA monomer, MHA (dimers+oligomers) and optionally Met were determined (see methods given above).
FIG. 3

Figure 4:
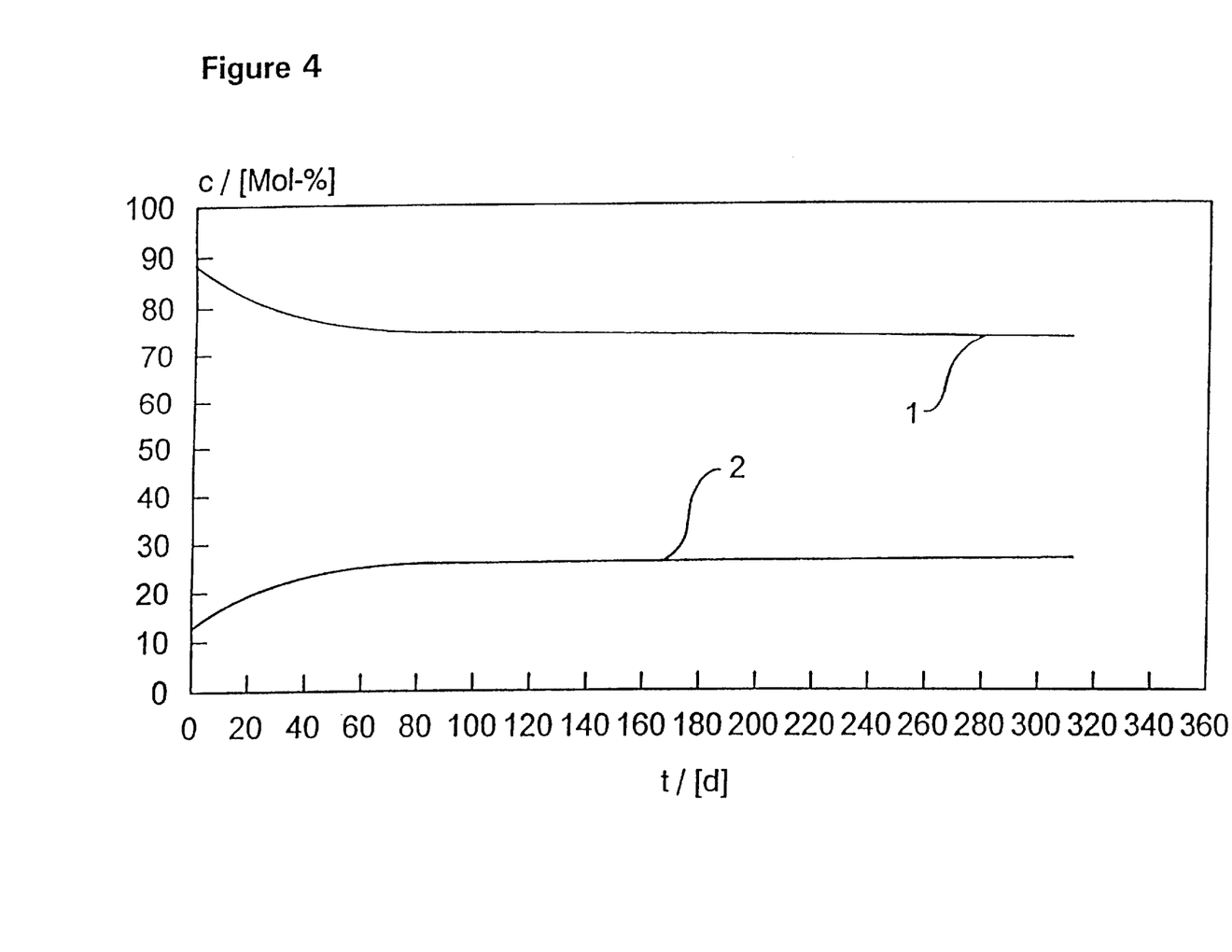
FIG. 4 a representation of the variation in concentration of MHA and dimers+oligomers in mol-% during the storage of MHA (88 wt. %) for 300 days at room temperature.

MHA concentrate which was prepared as in example 3, experiment 2, produced an equilibrium mixture, after about 3 month's storage at room temperature, of 47 mol-% MHA monomer (1) and
53 mol-% MHA (dimers+oligomers) (2).
FIG. 4

Figure 5:
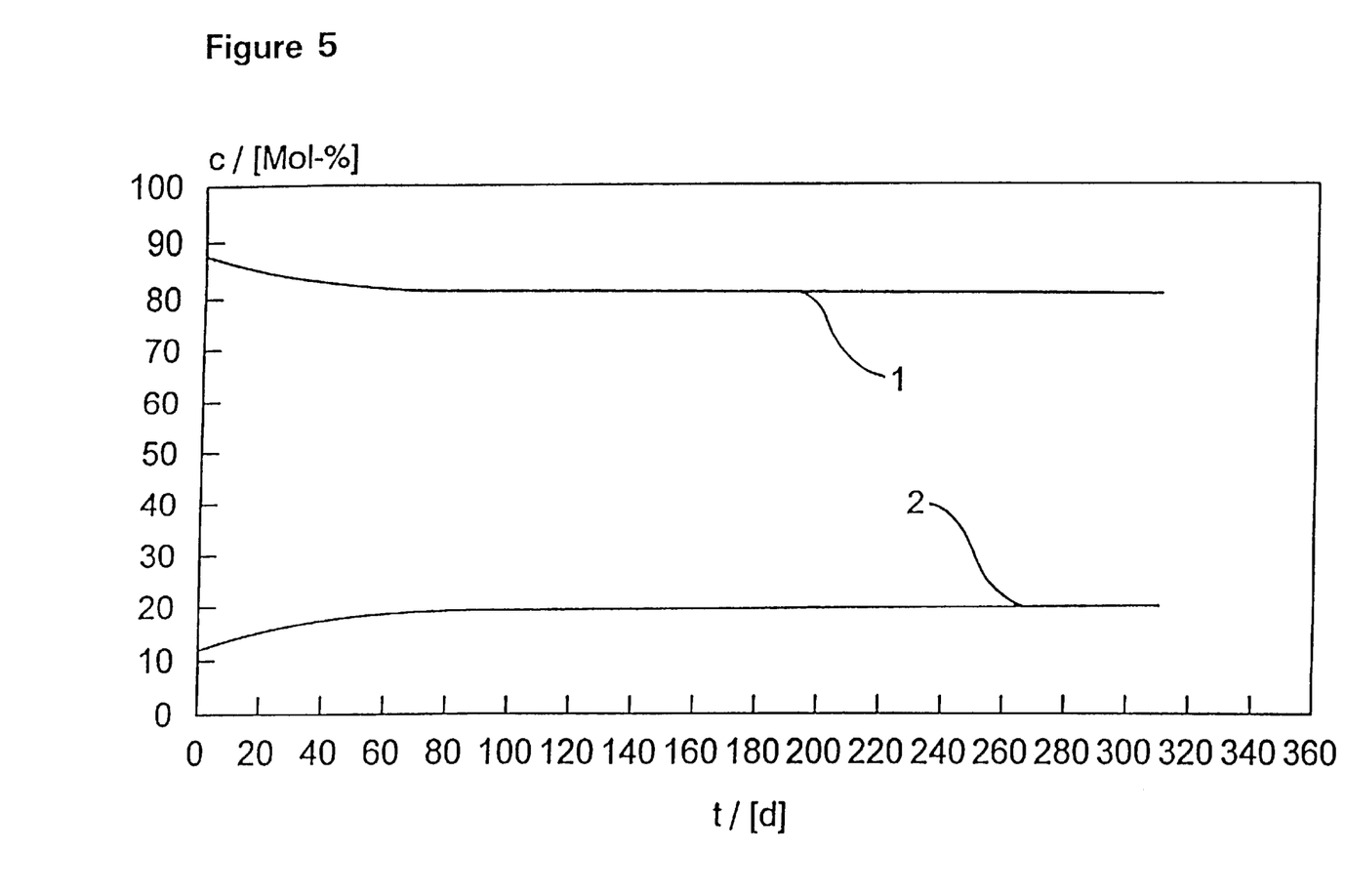
FIG. 5 a representation of the variation in MHA+ methionin, dimers+oligomers and the methionin content in mol-% during the storage of MHA mixtures of 78 wt. % of MHA and 10 wt. % of methionin for 300 days at room temperature.

MHA 88, which was prepared in the same way as in example 3, experiment 2 and then diluted with water to 88% MHA content, produced an equilibrium mixture, after about 3 months storage at room temperature, of 74 mol-% MHA monomers (1)
26 mol-% MHA dimers+oligomers (2)
This ratio was also found in commercial products.
FIG. 5

Figure 6:
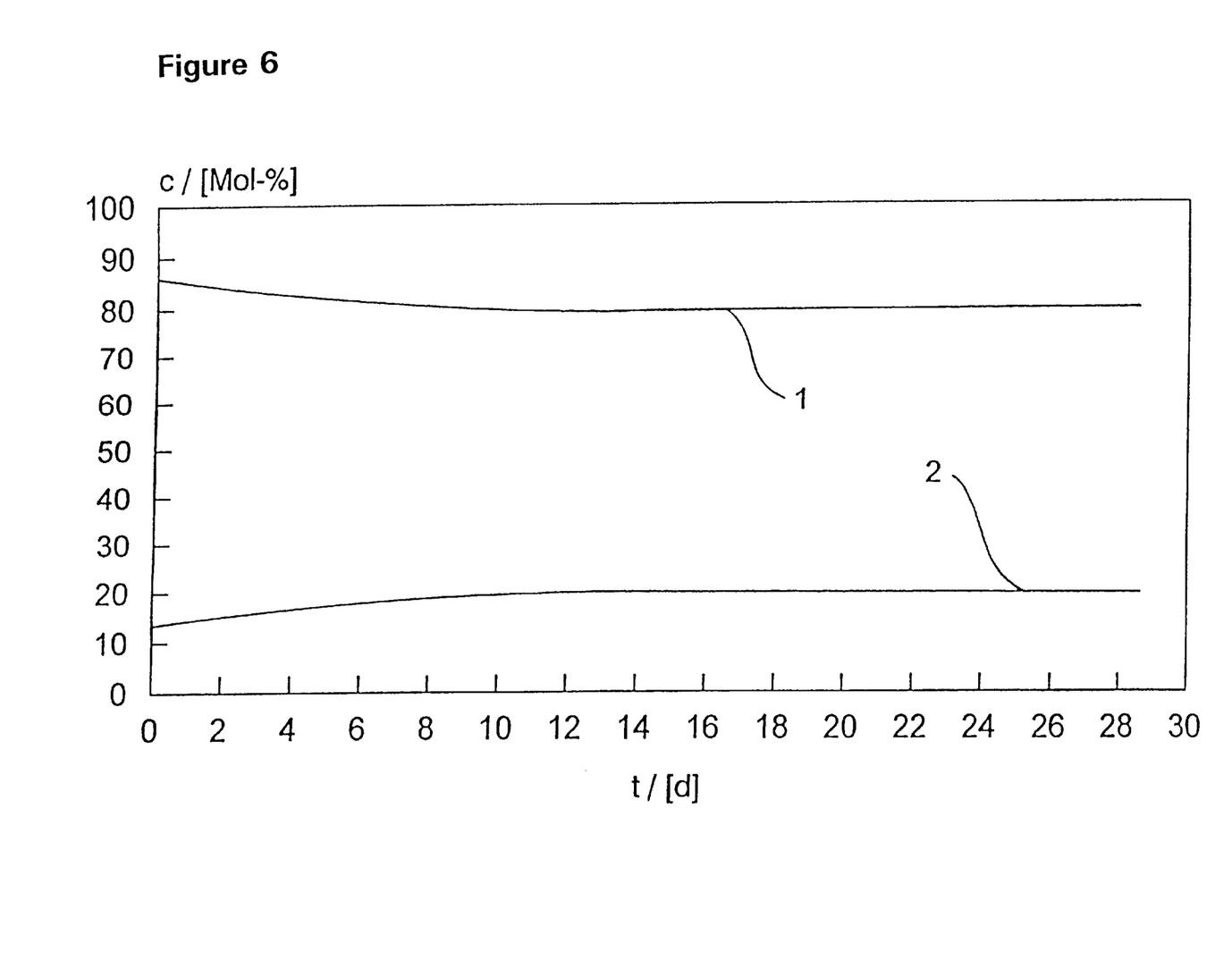
FIG. 6 a representation of the variation in MHA+ ammonium MHA, dimers+oligomers, and ammonium MHA content in mol-% during the storage of MHA mixtures of 78 wt. % MHA+10 wt. % of ammonium MHA for 30 days at 40° C.

MHA 78+Met 10 which was prepared as in example 4, experiment 1 produced an equilibrium mixture, after about 3 months storage at room temperature, of 80 mol-% MHA monomer+Met (1)
20 mol-% MHA dimers+oligomers (2)
FIG. 6

MHA 78+MHANH4 10, which was prepared as in example 7, produced an equilibrium mixture, after only 14 days storage at 40° C., of 80 mol-% MHA monomers (1) and
20 mol-% MHA dimers+oligomers (2).

A comparison of FIGS. 3, 4, 5 and 6 shows that product mixtures such as MHA 78+Met 10 or MHA 78+MHANH$_4$ 10 clearly have more favourable (dimers+oligomers)-fractions than commercial MHA 88 after prolonged storage. With MHA 78+MHANH$_4$ 10 the equilibrium state (caused by elevated temperature) was reached (FIG. 6) much earlier than in the other cases shown.

We claim:

1. A process for recovering 2-hydroxy-4-methylthiobutyric acid (MHA) in which the MHA is isolated from a reaction mixture comprising:
   a) adding hydrocyanic acid (HCN) to methylmercaptopropionaldehyde (MMP) to obtain methylmercaptopropionaldehyde cyanohydrin (MMP-CH),
   b) hydrolyzing the thereby obtained methylmercaptopropionaldehyde cyanohydrin (MMP-CH) in a first stage with 60–85% strength sulphuric acid in a molar ratio MMP-CH:H$_2$SO$_4$ of 1:0.5 to 1:1.05 at temperatures of 30–90° C. with the production of essentially MHA-amide, and in a second stage by adding water without the further addition of H$_2$SO$_4$ at temperatures of up to 140° C.,
   c) adding an organic solvent which is essentially immiscible with water to the reaction mixture in a liquid/liquid extraction system,
   d) thereby forming an extraction solution which contains the solvent and MHA transferred from the reaction mixture, and
   e) obtaining the MHA as an extract from said extraction solution by evaporation, by using a thin layer evaporator, or a falling film evaporator or a short-path evaporator or a short-path evaporator and a stripping stage or a stripping stage;
   f) wherein the evaporation is performed in such a way that the remaining extract contains less than 4 wt. % of water;
   g) obtaining MHA containing ≦10 mol-% dimers and oligomers.

2. A process according to claim 1, wherein pressure during evaporation is not greater than 600 mbar.

3. A process according to claim 1 wherein temperature of the MHA as an extract during evaporation is not essentially higher than 150° C.

4. A process according to claim 3, wherein temperature of the MHA as an extract is between 30 and 100° C. at an outlet from the evaporation procedure.

5. A process according to claim 1 wherein residence time of the remaining extract in evaporation stage is not longer than 1.5 h.

6. MHA obtained according to the process of claim 1, having more than 98 wt. % of MHA calculated as the sum of monomeric MHA, MHA dimers and MHA oligomers as well as more than 0.1 and less than 2 wt. % of water and a kinematic viscosity of >100 mm$^2$/s at 25° C.

7. Mixtures for supplementing animal feedstuffs comprising a mixture of methionin and MHA according to claim 6 wherein MHA content including monomers, dimers and oligomers is <80 wt. % and wherein oligomer content including MHA dimers and oligomers is <25 mol-%, with respect to total active substance content of MHA, dimers and oligomers and methionin, after storage for 300 days at room temperature.

8. A mixture for supplementing animal feedstuffs, comprising MHA according to claim 6 wherein the MHA content including monomers, dimers and oligomers is <80 wt. % and wherein oligomer content including MHA dimers and oligomers is <25 mol-%, with respect to total active substance content of MHA, dimers and oligomers, after storage for 30 days at 40° C.

* * * * *